United States Patent [19]

House, Sr.

[11] Patent Number: 4,660,562
[45] Date of Patent: Apr. 28, 1987

[54] MULTI-EVENT BIOMEDICAL ELECTRODE ASSEMBLY

[76] Inventor: Hugh A. House, Sr., P.O. Box 938, Rockwell, N.C. 28138

[21] Appl. No.: 709,294

[22] Filed: Mar. 7, 1985

[51] Int. Cl.$^4$ ............................................. A61B 5/04
[52] U.S. Cl. .................................. 128/640; 128/641; 128/670; 128/734; 128/736
[58] Field of Search ............... 128/639, 640, 641, 670, 128/700, 734, 736

[56] References Cited

U.S. PATENT DOCUMENTS

| | | | |
|---|---|---|---|
| 3,870,034 | 3/1975 | James | 128/734 |
| 3,993,049 | 11/1976 | Kater | 128/640 |
| 4,016,869 | 4/1977 | Reichenberger | 128/640 |
| 4,090,504 | 5/1978 | Nathan | 128/670 |
| 4,538,617 | 9/1985 | Jensen | 128/641 |

*Primary Examiner*—Kyle L. Howell
*Assistant Examiner*—Randy Citrin
*Attorney, Agent, or Firm*—Sachs & Sachs

[57] ABSTRACT

An electrode assembly for multi-event biomedical event measuring which has a device for sensing more than one physiological parameter of a patient and includes a housing having an upwardly extending portion adapted to receive a mating connector that includes a plurality of electrically conductive paths. The electrically conductive paths are positioned to coincide with electrically conductive paths provided in the upwardly extending housing portion. The housing base includes at least a plurality of compartments; at least one of the compartments circumferentially surround the upwardly extending portion and is open in the opposite direction therefrom. The remaining compartments are disposed beneath the upwardly extending portion and are also open in the opposite direction therefrom. Each of the remaining compartments are adapted to receive a transducer therein with the transducer terminals being connected to the upwardly extending portion conductive paths. An adhesive pad having a centrally disposed aperture is adapted to receive the base portion of the housing therein and is retained in position by a retaining ring. An electrolyte gel is disposed in at least the circumferentially disposed compartment. A semi-permeable membrane is received by the base portion and covers all of the compartment openings.

11 Claims, 6 Drawing Figures

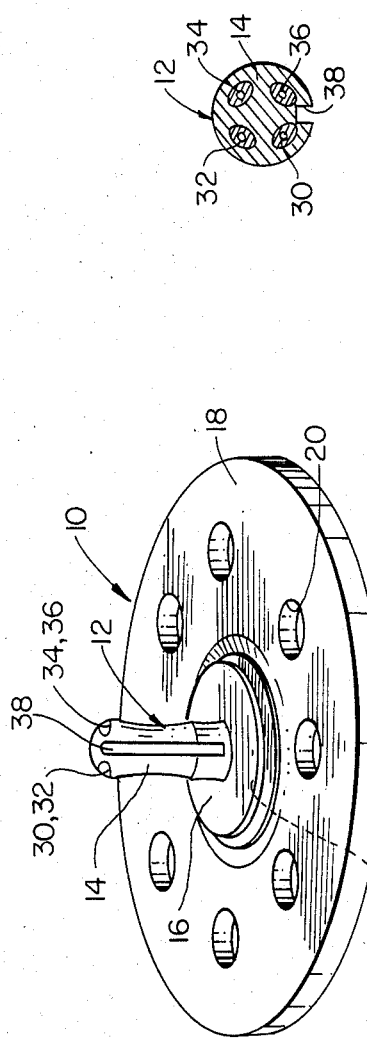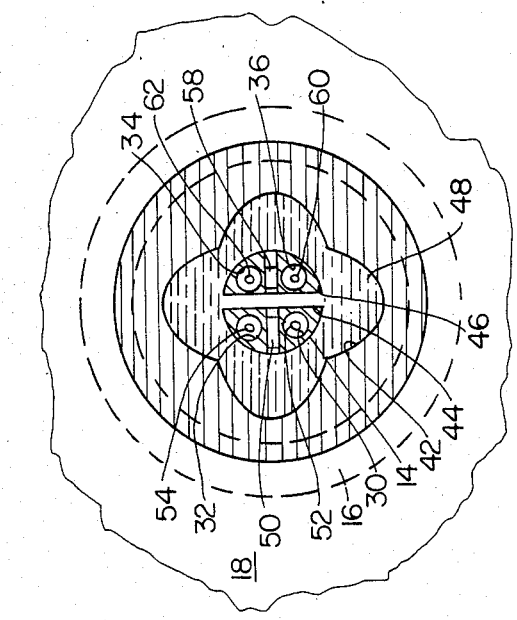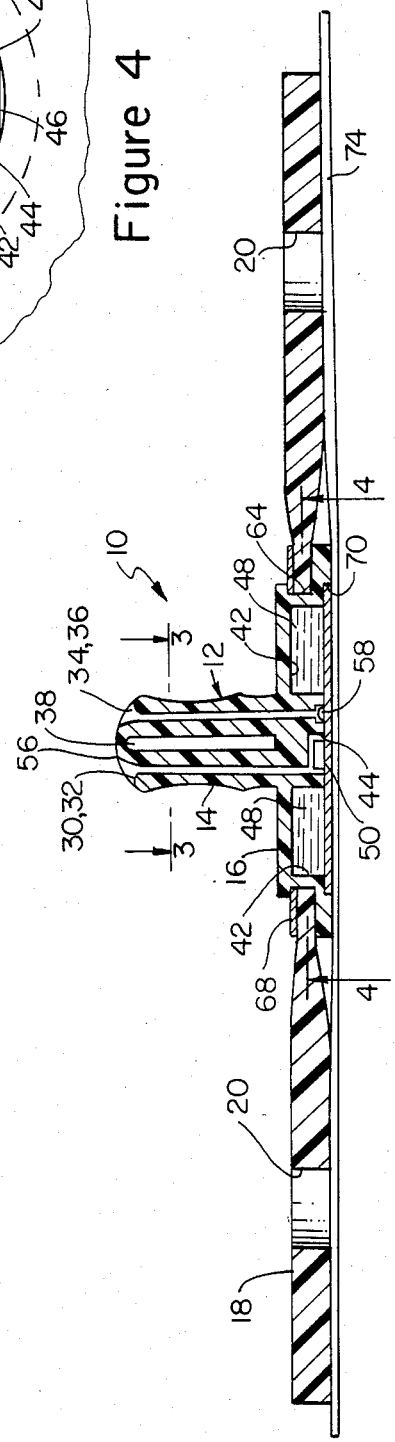

MULTI-EVENT BIOMEDICAL ELECTRODE ASSEMBLY

BACKGROUND OF THE INVENTION

1. Field of the Invention

The present invention relates to bio-electric event measuring electrodes, and in particular relates to a multi-event biomedical electrode assembly utilizing a plurality of electrodes and/or sensing more than one physiological parameter of a patient.

2. Discussion of the Relevant Art

The art abounds with medical electrodes that are designed to be affixed to the human body in order to obtain the electrical nerve impulses that the heart and brain generate and with which they respond. These low lever electrical signals can be detected using the appropriate medical electrodes that have good skin contact and very low resistivity. These electrodes must have high sensitivity and are usually placed directly on the skin to make very good electrical contact with the skin surface. Generally, an electrolyte is incorporated to increase the sensitivity of the electrode and reduce its resistivity when applied to the skin. These electrodes are generally held in place by an adhesive material which has as an adhering surface covered with a removable covering prior to application to a patient. Typical of these devices is the assembly disclosed in U.S. Pat. No. 4,350,165 issued to J. G. Striese on Sept. 21, 1982. However, this type of electrode can only be used to sense one physiological parameter since it is a single contact electrode and requires a plurality thereof to obtain the required conductors.

Attempts have been made to utilize a multi-electrode terminal such as that disclosed in U.S. Pat. No. 3,993,049 which issued to J. A. R. Kater on Nov. 23, 1976. The apparatus disclosed therein utilizes an assembly which has three electrodes disposed thereon and a connector affixed thereto that is provided with three conductive paths or wires. As dislcosed therein, one of the paths is generally used as a neutral or ground conductor when it is connected to a measuring apparatus. Here again, although multi-electrodes are utilized only a single electrical type of electrode terminal is obtainable.

Therefore, it is an object of the present invention to overcome the shortcomings of the relevant art by providing a multi-event biomedical electrode assembly.

It is yet another object of the present invention to provide a multi-event electrode that is capable of providing electrical output signals which may be used to record different-independent physiological parameters.

It is yet another object of the present invention to provide a multi-event electrode which may be utilized to provide two or more electrically conductive paths which may be used for different purposes.

It is still yet a further object of the present invention to provide a multi-event electrode which is fabricated from an epoxy conducting resin thereby reducing the cost of present day electrodes.

It is still yet another object of the present invention to provide a multi-event biomedical electrode assembly that has a housing that is electrically conductive and/or may provide a plurality of electrically conductive paths therein without using metal conductors.

It is still yet another object of the present invention to provide a multi-event biomedical electrode assembly that is capable of providing a temperature reading proximate the surface of the electrode, as well as, providing an electrical output signal voltage related to the electrical impulses provided to the heart for measuring pulse rate.

It is yet another object of the present invention to provide a multi-event biomedical electrode assembly capable of measuring the temperature on the surface proximate the location of the electrode on the skin of a patient.

It is still yet another object of the present invention to provide a multi-event biomedical electrode assembly that is capable of providing an electrical output relative to the pH of the skin and by combining it with other measuring devices can be used to provide an output relative to blood pressure.

It is still yet another object of the present invention to provide a multi-event biomedical electrode assembly that is capable of providing independent channels which may be used individually and/or simultaneously.

SUMMARY OF THE INVENTION

A multi-event biomedical electrode assembly for simultaneously sensing more than one physiological parameter of a patient, according to the principles of the present invention, comprises in combination; a housing having an upwardly extending portion adapted to receive a mating connector thereon and includes a plurality of electrically conductive paths disposed therein. The conductive paths are positioned to coincide with electrically conductive paths provided in a mating connector. The base portion of the housing is provided with a plurality of compartments; at least one of the compartments circumferentially surrounds the upwardly extending portion and is open in the opposite direction therefrom. The remaining compartments are disposed beneath the upwardly extending portion and are also open in the opposite direction therefrom. Each of the remaining compartments are adapted to receive a transducer therein. The conductive terminals of the tranducers are connected to the upwardly extending portion conductive paths. An adhesive member having a centrally disposed aperture therein is adapted to receive the base portion of the housing and is retained therein by a ring member. An electrolyte gel is disposed in at least the circumferentially disposed compartment with a membrane covering all the compartments disposed in the base member. A removable cover protects the adhesive surface and membrane from contact with the air, maintaining it free from contamination.

The foregoing and other objects and advantages will appear from the description to follow. In the description reference is made to the accompanying drawing which forms a part hereof, and in which is shown by way of illustration a specific embodiment in which the invention may be practiced. This embodiment will be described in sufficient detail to enable those skilled in the art to practice the invention, and it is to be understood that other embodiments may be utilized and that structural changes may be made without departing from the spirit and scope of the invention. The following detailed description is, therefore, not to be taken in a limiting sense, and the scope of the present invention is best defined by the appended claims.

BRIEF DESCRIPTION OF THE DRAWING

In order that the invention may be more fully understood, it will now be described, by way of example, with reference to the accompanying drawing in which:

FIG. 1 is a perspective view of the multi-event biomedical electrode assembly, according to the principles of the present invention;

FIG. 2 is an enlarged cross-section view of the multi-event biomedical electrode assembly;

FIG. 3 is a sectional view taken along the line 3—3 of FIG. 2;

FIG. 4 is a partial bottom view of the multi-event electrode assembly with the protective covering removed.

BRIEF DESCRIPTION OF THE DRAWING

Figure 5:
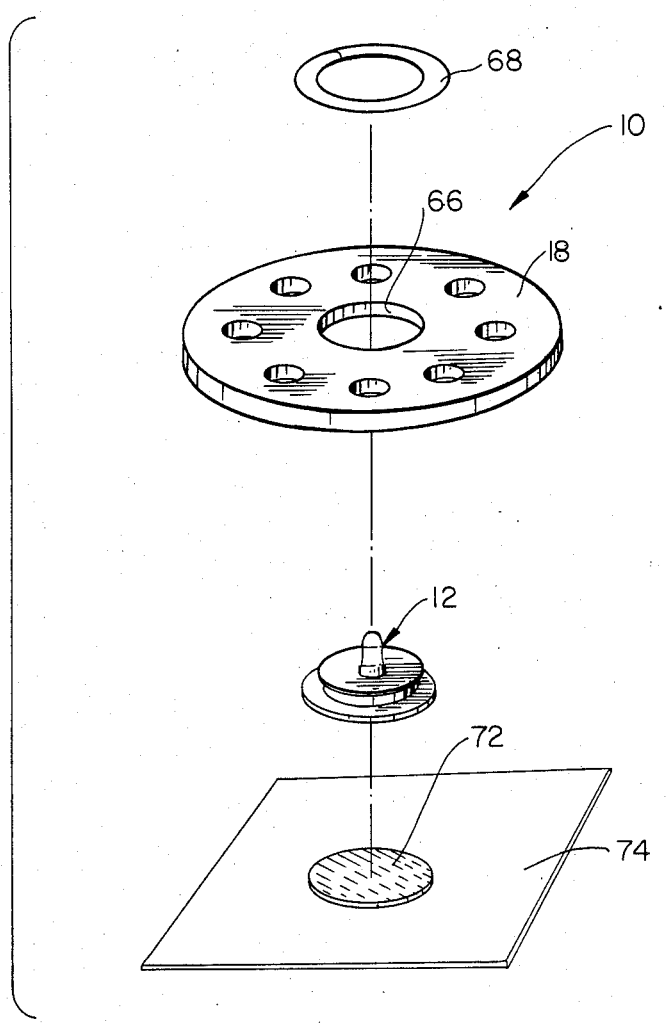
FIG. 5 is an exploded perspective view of the multi-event biomedical electrode assembly.

Referring now to the figures, and in particular to FIGS. 1 through 4, there is shown a multi-event biomedical electrode assembly 10 that includes an electrode housing 12 having a cylindrically shaped upwardly extending portion 14 and a base portion 16 that is surrounded by a disc-shaped outwardly extending adhesive member 18 that is provided with a plurality of apertures 20 equally disposed about the surface area in order to provide venting when affixed to the skin of a patient, not shown.

Figure 6:
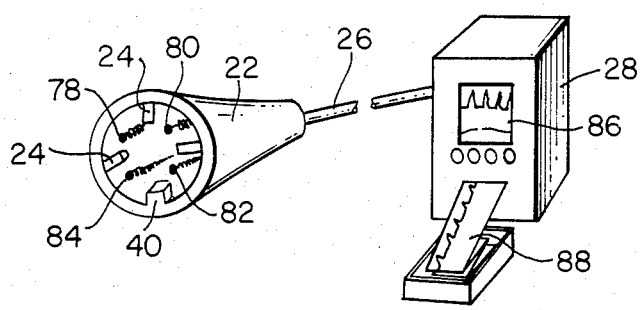
FIG. 6 is a pictorial representation of a mating connector plug and recording apparatus associated therewith, not drawn to scale.

In one embodiment of the invention the upwardly extending portion or plug 124 and the base portion 16 are fabricated as a unitary structure utilizing an electrically conductive epoxy resin. Thus, since the material utilized is electrically conductive a mating receptacle 22 (see FIG. 6) may include a plurality of electrically conductive fingers 24 to continue the electrically conductive path from the outer surface of the upwardly extending portion or plug 14 through the contact fingers 24, via cable 26 to the apparatus 28 that uses the electrical information as will be explained hereinafter.

In an alternative embodiment wherein the upwardly extending plug portion 14 and base portion 16 are fabricated from a non-conductive epoxy resin a conductive current path may be provided by using conductive epoxy resin or wire having an insulated sleeve thereover inserted within the apertures or channels 30, 33, 34 and 36 provided in the upwardly extending front portion 14. Additionally, the upwardly extending portion 14 is provided with an indexing channel 38 which is adapted to receive and cooperate with protrusion 40 provided on mating receptacle 22.

The underside of the base portion 16 is provided with a plurality of compartments 42, 44 and 46 which are disposed beneath the upwardly extending plug portion 14. Compartment 42 circumscribes the upwardly extending plug portion 14 and is preferably provided with a conductive electrolyte gel 48. Disposed in compartment 44 is a miniaturized audio transducer 50 that is provided with a pair of conductive terminals or wires 52 and 54 that extend upwardly, via the channels 30 and 32 until they reach the distal edge 56 of upwardly extending plug 14. If the plug 14 is fabricated with an insulated epoxy resin then the conductive epoxy resin is poured into apertures 30 and 32 forming an electrically conductive path between the terminals or wires 52 and 54 of the audio transducer 50 and the distal edge 56 of the plug 14. The conductive epoxy will also serve to hold the audio transducer into position in the compartment 44.

If a conductive epoxy resin is used to fabricate the housing 12, an insulated sleeve is inserted over the wire or terminal 52 which is made to extend within the channel 30 to distal edge 56. Electrically condUCtive epoxy is poured into the opening provided in the insulated sleeve, thus providing an electrically conductive path in that manner to distal edge 56. The housing of the audio transducer 50 may be placed in electrical contact with the housing 12 and affixed thereto with a small amount of conductive epoxy and a second terminal or lead will not be required, since the output therefrom can be obtained across terminal 52 and the surface of the housing 12.

Inserted in compartment 44 is a thermistor 58 which, as is well known, is a temperature sensitive resistor ideally suitable for monitoring temperature in the area proximate thereto since its resistance is responsive to the temperature of its environment. The thermistor terminals or wires 60 and 62 are threaded through channels 34 and 36 in a manner similar to that utilized for the audio transducer 50, thereby providing the electrical conductive path required once the conductive epoxy is poured into the channels 34 and 36. Hereagain, if the housing is made of the conductive epoxy only one lead need be channeled through aperture 34, since the second terminal will be the common surface of the electrode housing as mentioned earlier. The unused channels may be used for an electrically conductive terminal contact with the skin of the individual by merely inserting an electrically conductive disc on the end of a wire or a conductive path provided by conductive epoxy poured into the vacant channel. Although only two transducers have been suggested for use in the instant embodiment, it is apparent by those knowledgeable in the art that any of a multitude of different transducer types may be incorporated in a similar manner.

The base portion 12 is provided with a circumferentially disposed U-channel 64 which is adapted to be received in an aperture 66 provided in the adhesive member 18 and by insertion of a split stainless steel washer 68 in the U-channel 68 and compressing the adhesive member 18, the adhesive member is retained by the base portion 16 and thus functions as a unitary member. The base portion 12 is further provided with a lip 70 on to which a semi-permeable membrane 72 is placed to cover each of the compartments into which the conductive electrolyte gel 48 is placed. Thus, the gel is only permitted to flow through the membrane on to the skin of an individual completing the conductive path when it is placed thereon. A removable cover 74 preferably of a waxed or non-sticking paper material temporarily adheres to the adhesive material to prevent contamination thereon and seals the unit from external contamination. As configured, the instant embodiment is capable of being sterilized and maintained in a sterile condition prior to use.

By utilizing the receptacle 22 (shown in FIG. 6) which meets with the upwardly extending plug portion 14 the electrical conductive paths are extended through the plug 14 through receptacle 22, via spring loaded pin contacts 78, 80, 82 and 84 and cable 26 to the electronic apparatus 28 wherein the signal information is processed, in a conventional manner to provide either a current visual display 86 or a paper tape continuous record 88.

Thus, as hereinbefore described the electrode may be utilized to measure the temperature appearing on the surface of an individual or by monitoring the heart sounds, the pulse rate can be readily determined. By using an external means for cutting off the circulation, such as a pressure cuff used on one of the extremities the systolic and diastolic pressure readings may be obtained.

In operation, the electrode will be placed on the skin of a patient after removing the protective paper covering 74. The adhesive 18 readily adheres to the patient's skin and the vent holes 20 provided will insure minimal, if any, irritation to the patient. The conductive gel seeps through the semi-permeable membrane 72 and insures good electrical and thermal contact with the skin for the conductive electrodes or any other transducer utilized in the compartments. The electrical signal voltages generated by the transducers are coupled through the plug portion 14, via receptacle 22, to the utilizing apparatus 28 which translate the electrical signals into readings in terms of the parameters they represent and will provide an instant visual display or a permanently recorded record.

FIG. 5 is an exploded view of the components disclosed in the multi-event biomedical electrode assembly and they are assembled in the manner shown, with the electrode housing 12 being inserted through aperture 66 of the adhesive member 18 and is retained therein by the ring member 78. These transducers having had their terminals earlier inserted into the channels provided in housing 12 which were filled with conductive epoxy. The electrolytic gel is applied to the compartments in housing 12 and which is then covered with a semi-permeable membrane 72. The protective covering 74 for the adhesive member 18 may then be applied to seal off the adhesive member and semi-permeable membrane from any contaminants.

Hereinbefore has been disclosed a multi-event biomedical electrode assembly that is capable of providing more than one physiological parameter of a patient either sequentially or simultaneously and is inexpensive enough to be disposable.

Having thus set forth the nature of the invention, what is claimed is:

1. A multi-event biomedical electrode assembly for simultaneously sensing more than one physiological parameter of a patient comprising, in combination:
   (a) housing means having;
      (i) an upwardly extending portion including means for receiving a mating connector thereon, and
      (ii) a plurality of electrically conductive paths disposed in said receiving means, said conductive paths being positioned to coincide with electrically conductive paths provided in a mating connector; and
   (b) a base portion having;
      (i) a plurality of compartments, at least one of of said compartments circumferentially surrounding said upwardly extending portion and open in the opposite direction therefrom, the remaining compartments being disposed beneath said upwardly extending portion and open in the opposite direction therefrom, each of said remaining compartments including means receiving a transducer having at least one conductive terminal, said transducer conductive terminal being connected to one of said receiving means conductive paths;
   (c) adhesive means having a centrally disposed aperture for receiving said base portion;
   (d) retaining means for retaining said base portion within said adhesive means aperture;
   (e) electrolyte means disposed in at least said circumferentially disposed compartment; and
   (f) membrane means for receiving said base portion covering all of said compartment openings.

2. A multi-event biomedical electrode assembly according to claim 1 further including removable cover means, said cover means covering and extending beyond said adhesive means to protect the adhesive from becoming contaminated and loosing its adhering ability.

3. A multi-event biomedical electrode assembly according to claim 1 wherein said housing means is fabricated from a conductive epoxy resin.

4. A multi-event biomedical electrode assembly according to claim 1 wherein said receiving means electrically conductive paths are fabricated from a conductive resin.

5. A multi-event biomedical electrode assembly according to claim 1 wherein said base portion includes a U-shaped circumferentially disposed edge channel adapted to receive said adhesive means aperture and said retaining means.

6. A multi-event biomedical electrode assembly according to claim 1 wherein receiving means of said housing means is provided with an indexing channel adapted to cooperate with a protrusion provided on a mating connector to insure proper continuation of said electrically conductive paths.

7. A multi-event biomedical electrode assembly according to claim 1 further including:
   (a) receptacle means removably received by and cooperating with said receiving means to continue said electrically conductive paths; and
   (b) apparatus means connected to said receptacle means for receiving electrical signals from said electrically conductive paths and utilizing said signals to provide a display or permanent record.

8. A multi-event biomedical electrode assembly for simultaneously sensing more than one physiological parameter of a patient comprising, in combination:
   (a) housing means having;
      (i) an upwardly extending portion including means for receiving a mating connector thereon, and
      (ii) a plurality of electrically conductive paths disposed in said receiving means, said conductive paths being positioned to coincide with electrically conductive paths provided in a mating connector;
   (b) a base portion having;
      (i) a plurality of compartments, at least one of said compartments circumferentially surrounding said upwardly extending portion and open in the opposite direction therefrom, the remaining compartments being disposed beneath said upwardly extending portion and open in the opposite direction therefrom;
   (c) adhesive means having a centrally disposed aperture for receiving said base portion;
   (d) retaining means for retaining said base portion within said adhesive means aperture;
   (e) electrolyte means disposed in at least said circumferentially disposed compartment;
   (f) membrane means for receiving said base portion covering all of said compartment openings; and (g) at least one transducer disposed within one of said remaining compartments, said transducer having at least one conductive terminal, one of said transducer conductive terminals being connected to one of said receiving means conductive paths.

9. A multi-event biomedical electrode assembly according to claim 8 wherein at least one of said transducers includes means for changing the sound of a beating heart to an electrical signal voltage.

10. A multi-event biomedical electrode assembly according to claim 8 wherein at least one of said transducers includes means for changing its resistance responsive to the temperature appearing proximate said transducer.

11. A multi-event biomedical electrode assembly according to claim 8 wherein at least one of said transducers includes means for measuring conductivity of the surface upon which said apparatus is affixed.

* * * * *

UNITED STATES PATENT AND TRADEMARK OFFICE
CERTIFICATE OF CORRECTION

PATENT NO. : 4,660,562

DATED : April 28, 1987

INVENTOR(S) : Hugh A. House, Sr.

It is certified that error appears in the above-identified patent and that said Letters Patent is hereby corrected as shown below:

<u>In the Specification:</u>

Column 3; line 34; delete the numeral "124" and insert therefor the numeral --14--.

Column 1; line 17; delete "lever" and insert therefor --level--.

Column 4; line 8; delete "condUCtive" and insert therefor --conductive--.

Column 5; line 32; delete the numeral "78" and insert therefor the numeral --68--.

Signed and Sealed this

Twelfth Day of January, 1988

Attest:

DONALD J. QUIGG

*Attesting Officer*   *Commissioner of Patents and Trademarks*